(12) United States Patent
Smith

(10) Patent No.: US 7,067,547 B1
(45) Date of Patent: Jun. 27, 2006

(54) OPHTHALMIC AND CONTACT LENS SOLUTIONS COMPRISING IMIDAZOLE

(75) Inventor: Francis X. Smith, Salem, NH (US)

(73) Assignee: FXS Ventures, LLC, Salem, NH (US)

( * ) Notice: Subject to any disclaimer, the term of this patent is extended or adjusted under 35 U.S.C. 154(b) by 0 days.

(21) Appl. No.: 09/706,318

(22) Filed: Nov. 4, 2000

Related U.S. Application Data

(60) Provisional application No. 60/163,453, filed on Nov. 4, 1999.

(51) Int. Cl.
  *A61K 31/415* (2006.01)
(52) U.S. Cl. ..................... 514/396; 514/912
(58) Field of Classification Search ............... 514/396, 514/912
  See application file for complete search history.

(56) References Cited

U.S. PATENT DOCUMENTS 6,162,393 A * 12/2000 De Bruiju .................... 422/28

\* cited by examiner

*Primary Examiner*—Zohreh Fay
(74) *Attorney, Agent, or Firm*—Hiscock & Barclay, LLP

(57) ABSTRACT

The present invention relates to contact lens solutions employing imidazole as an additive. Lenses treated with these solutions have improved resistance to protein and other polymeric depositions. The addition of imidazole to the solutions decreases the denaturalization of proteins during the cleaning cycles, and coats treated lenses to decrease the number of active binding sites.

22 Claims, No Drawings

OPHTHALMIC AND CONTACT LENS SOLUTIONS COMPRISING IMIDAZOLE

This application claims the benefit of Provisional Application No. 60/163,453, filed Nov. 4, 1999.

SUMMARY OF THE INVENTION

The present invention relates to contact lens care solutions that have improved ability to resist protein deposition and to provide lenses treated with such solutions to stabilise proteins more effectively, and to decrease the degree of other polymeric depositions on said lenses, such as polymeric preservative deposition of the lenses. The solutions of the present invention employ imidazole as an additive to state of the art solutions in order to decrease the denaturalization of proteins during cleaning cycles and to coat treated lenses to decrease the number of active binding sites on the lenses.

The present invention comprises 0.01 to 5 weight percent of imidazole and a second contact lens solution agent. These agents may include but are not limited to includes an effective amount of a preservative component, for example, an effective preserving amount of a non-oxidative antimicrobial component. Any suitable preservative component may be employed provided that it functions as a preservative and has no significant detrimental effect on the contact lens being treated or the wearer of the treated contact lens. Examples of useful preservative components include, but are not limited to, poly[dimethylimino-2-butene-1,4-diyl] chloride, alpha [4-tris (2-hydroethyl) anunoniumdichloride (available from Onyx Corporation under the trademark Polyquai-ternium 1 Registered TM), benzalkonium halides such as benzalkonium chloride, alexidine salts, chlorhexidine salts, hexamethylene biguanimides and their polymers, and the like and mixtures thereof.

The subtilisin enzymes are broken down into two subclasses, subtilisin A and subtilisin B. In the subtilisin A grouping are enzymes derived from such species are *B. subtilis, B. liceniformis* and *B. pumilis*. Organisms in this sub-class produce little or not neutral protease or amylase. The subtilisin B. sub-class is made up of enzymes from such organisms a *B. subtilis, B. subtilis* var. *amylosacchariticus, B. amyloliquefaciens* and *B. subtilis* NRRL B341 1. These organisms product neutral proteases and amylases on a level about comparable to their alkaline protease production. One or more enzymes from the subtilisin A sub-class are particularly useful.

In addition other preferred enzymes are, for example, pancreatin, trypsin, collagenase, keratinase, carboxylase, aminopeptidase, elastase, and aspergillo-peptidase A and B, pronase E (from *S. griseus*) and dispase (from *Bacillus polymyxa*).

An effective amount of enzyme is to be used in the practice of this invention. Such amount will be that amount which effects removal in a reasonable time (for example overnight) of substantially all of at least one type of debris from a lens due to normal wear. this standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.00 1 to about 3 Anson units of activity, preferably about 0.01 to about 1 Anson units, per single lens treatment. Higher or lower amounts may be used. Enzyme activity is pH dependent so for any given enzyme, there is a particular pH range that is most effective and the solution may be formulated to adjust the pH for optimal enzyme activity.

EXAMPLE

Reduced Protein Deposition

Contact lenses were soaked and heated in test solutions to which a radio-labeled lysozyme was present in a known amount for a period of 12 hours at 37 degrees Celsius. The lenses were rinsed with distilled water in order to remove residual solution. The lenses were then assayed for protein deposition using a Beckman BioGamma 1 counter. Results were reported in ug/lens.

|  | Lens A ug/lens | Lens B ug/lens | Average ug/lens |
| --- | --- | --- | --- |
| Phosphate buffer control | 1,043 | 865 | 954 |
| 1% Imidazole | 16 | 11 | 14 |

The imidazole was a 1 percent w/v solution. The matrix control was phosphate buffer and sodium chloride. The imidazole-hydrogen peroxide solution had lower protein binding than the control.

EXAMPLE

Reduced Preservative Binding

Contact lenses were soaked and heated in test solutions to which a radio-labeled $C^{14}$-PHMB solution in a known concentration for a period of 12 hours at 37 degrees Celsius. The lenses were rinsed with distilled water in order to remove residual solution. The lenses were then assayed for the radio-labeled protein deposition using a Beckman BioGamma 1 counter. Results were reported in ug/lens.

| Solution | Lens A ug/lens | Lens B ug/lens | Average ug/lens |
| --- | --- | --- | --- |
| 1% imidazole in phosphate buffer | 21 | 17 | 19 |
| Phosphate buffer control | 73 | 64 | 68.5 |

The imidazole was at a 1 percent w/v solution in the phosphate buffer. The control was phosphate buffer and sodium chloride. The imidazole solution had a lower cationic preservative adsorption than the control.

EXAMPLE

Inhibition of Protein Deposition

Isotonic aqueous phosphate buffered solutions were prepared and adjusted to pH 7.4. Contact lenses were soaked in 25 mL of the test solutions overnight. Afterwards, lysozyme was added to the tubes and warmed to 37 degrees Celsius for 12 hours. The lenses were rinsed with distilled water in order to remove residual solution. The lenses were assayed for protein deposition by the BCA method and detected on a HP PDA Spectrophotometer. Results were reported in ug/lens.

| Solution | ug lysozyme per lens |
| --- | --- |
| Marketed Product Control (phosphate buffer, Poloxamer) | >18.3 |
| Phosphate buffer control | >26.16 |
| 1% Imidazole - hydrogen peroxide | 3.52 |

The matrix control was phosphate buffer and sodium chloride. The imidazole solution had lower protein binding than the controls.

EXAMPLE

Protein Stability (Experiment BCL075-126)

Test solutions were prepared according to the formulas indicated in the table had undenatured protein added in a control and were heated to approximately 80 degrees Celsius as indicated. Each sample was observed for clarity. This test provides useful results for indicating the protein is stabilized in comparison with other solutions subjected to the same test regimen.

| | Weight | | | | | | | | |
| --- | --- | --- | --- | --- | --- | --- | --- | --- | --- |
| Solution | 10 80° C. 15 min | 8 80° C. 30 min | 7 80° C. 45 min | 6 80° C. 60 min | 4 Ambient 15 min | 3 Ambient 30 min | 2 Ambient 24 hour | 1 Ambient 48 hour | Total |
| I | 0 | 0 | 0 | 1 | 2 | 2 | 3 | 3 | 29 |
| II | 1 | 2 | 3 | 3 | 3 | 3 | 3 | 3 | 95 |
| III | 3 | 3 | 3 | 3 | 3 | 3 | 3 | 3 | 123 |
| IV | 0 | 1 | 3 | 3 | 3 | 3 | 3 | 3 | 77 |
| V | 1 | 3 | 3 | 3 | 3 | 3 | 3 | 3 | 103 |
| VI | 1 | 3 | 3 | 3 | 3 | 3 | 3 | 3 | 103 |

I. 1% imidazole in phosphate buffer
II. phosphate buffer control
III. marketed product having the general composition: A sterile, aqueous, buffered, slightly hypertonic solution containing PEO sorbitan monolaurate and a betaine surfactant as cleaning agents; a slilicone glycol copolymer, a cellulosic viscosifier preserved with chlorhexidine gluconate (0.003%), polyaminopropyl biquanide (0.0005% and edetate disodium (0.05%).
IV. marketed product having the general composition: A sterile, isotonic solution that contains boric acid, edetate disodium, poloxamine, sodium borate and sodium chloride; preserved with DYMED (polyaminopropyl biquanide) 0.00005%.
V. marketed product having the general composition: A sterile, isotonic solution that contains HYDRANATE (hydroxyalkylphosphonate), boric acid, edetate disodium, poloxamine, sodium borate and sodium chloride; preserved with DYMED (polyaminopropyl biquanide) 0.0001%.
VI. marketed product having the general composition: A sterile isotonic aqueous solution containing sodium chloride, polyoxyethylene polyoxypropylene block copolymer, sodium phosphate dibasic, sodium phosphate monobasic, and preserved with edetate disodium dihydrate 0.025% and polyhexanide 0.0001%.

A weighting factor as indicated in the table was used to multiply each result. 0 indicated a clear sample; 1 slightly turbid, 2 turbid, and 3 indicated cloudy and separate phases (precipitate). The data illustrates the ability of imidazole to stabilize the protein and thus decrease the extent of opacification on the contact lens from the protein deposit. The formula performed superior to the marketed products.

What is claimed is:

1. A lens care solution comprising:
an aqueous solution comprising 0.01 to about 5 weight percent imidazole; an effective amount of a preserving agent; and the balance water.

2. The lens care solution of claim 1 wherein the aqueous solution further comprises the 1,2-bis[tris(hydroxymethyl)-methylamino}propane (Bis-Tris Propane) and its salts.

3. The lens care solution of claim 1 wherein the aqueous solution further comprises the N-tris(hydroxymethyl) methyl glycine (Tricine) and its salts.

4. The lens care solution of claim 1 wherein the aqueous solution further comprises the N,N-bis(2-hydroxyethyl)-glycine (Bicine) and its salts.

5. The lens care solution of claim 1 wherein the aqueous solution further comprises the betaine and its salts.

6. The lens care solution of claim 1 wherein the aqueous solution further comprises the buffer phosphate and its salts.

7. The lens care solution of claim 1 wherein the aqueous solution further comprises the buffer is borate and its salts.

8. The lens care solution of claim 1 wherein the aqueous solution further comprises the is citrate and its salts.

9. The lens care solution of claim 1 wherein the aqueous solution further comprises is TRIS and its salts.

10. The lens care solution of claim 1 wherein the aqueous solution further comprises the buffer is 2-amino-2-methyl-1,3-propanediol and its salts.

11. The lens care solution of claim 1 wherein the aqueous solution further comprises the buffer is triisopropanolamine and its salts.

12. The lens care solution of claim 1 wherein the aqueous solution further comprises the buffer is carnitine and its salts.

13. The lens care solution of claim 1 wherein the aqueous solution further comprises the buffer is dimethyl glutamate and its salts.

14. The lens care solution of claim 1 wherein the aqueous solution further comprises the buffer is creatine and its salts.

15. The lens care solution of claim 1 wherein the aqueous solution further comprises the buffer is diethanolamine and its salts.

16. The lens care solution of claim 1 wherein the aqueous solution further comprises the buffer is diisopropylamine and its salts.

17. The lens care solution of claim 1 wherein the aqueous solution further comprises the buffer is triethanolamine and its salts.

18. The lens care solution of claim 1 wherein the aqueous solution further comprises the buffer is triethylamine and its salts.

19. The lens care solution of claim 1 wherein the aqueous solution further comprises the buffer is dimethyl aspartic acid and its salts.

20. The lens care solution of claim 1 wherein the aqueous solution further comprises the buffer is imidazole and its salts.

21. The lens care solution of claim 1 wherein the aqueous solution further comprises the buffer is histidine and its salts.

22. The lens care solution of claim 1 wherein the aqueous solution further comprises the buffer is methyl aspartate and its salts.

* * * * *